United States Patent [19]

Fülberth et al.

[11] Patent Number: 4,552,771

[45] Date of Patent: Nov. 12, 1985

[54] ACESULFAM-CONTAINING COMPOSITION TABLETS ON THE BASIS THEREOF AND PROCESS FOR THE MANUFACTURE OF THESE TABLETS

[75] Inventors: Werner Fülberth, Kelkheim; Alfred Sickmüller, Frankfurt am Main; Willi Stammberger, Hofheim am Taunus, all of Fed. Rep. of Germany

[73] Assignee: Hoechst Aktiengesellschaft, Frankfurt am Main, Fed. Rep. of Germany

[21] Appl. No.: 554,163

[22] Filed: Nov. 21, 1983

Related U.S. Application Data

[63] Continuation of Ser. No. 348,966, Feb. 16, 1982, abandoned.

[30] Foreign Application Priority Data

Feb. 18, 1981 [DE] Fed. Rep. of Germany ....... 3105813

[51] Int. Cl.⁴ ............................................. A23L 1/236
[52] U.S. Cl. .................................... 426/548; 426/576; 426/454
[58] Field of Search ................ 426/548, 591, 576, 454

[56] References Cited

U.S. PATENT DOCUMENTS

| | | | |
|---|---|---|---|
| 3,061,445 | 10/1962 | Stanish | 426/548 |
| 3,173,797 | 3/1965 | Lowery | 426/548 |
| 3,875,311 | 4/1975 | Eisenstadt | 426/548 |
| 3,946,121 | 3/1976 | Eisenstadt | 426/548 |
| 4,004,036 | 1/1977 | Schmitt | 426/548 |
| 4,009,292 | 2/1977 | Finucane | 426/548 |
| 4,127,645 | 11/1978 | Witzel | 426/548 |
| 4,292,336 | 9/1981 | Latymer | 426/548 |

FOREIGN PATENT DOCUMENTS

| | | | |
|---|---|---|---|
| 2001017 | 7/1971 | Fed. Rep. of Germany | 426/548 |
| 551193 | 11/1970 | Switzerland . | |

OTHER PUBLICATIONS

Little et al., Tablet Making, Northern Pub. Co. Ltd., England, 1963, pp. 48–51.

*Primary Examiner*—Jeanette Hunter
*Attorney, Agent, or Firm*—Curtis, Morris & Safford

[57] ABSTRACT

Composition containing acesulfam or a salt thereof, a soluble, $CO_2$-yielding compound, optionally a physiologically acceptable acid as auxiliary, and gelatin powder as dry binder, and its use for the manufacture of tablets.

10 Claims, No Drawings

ACESULFAM-CONTAINING COMPOSITION TABLETS ON THE BASIS THEREOF AND PROCESS FOR THE MANUFACTURE OF THESE TABLETS

This application is a continuation of application Ser. No. 348,966, filed Feb. 16, 1982, abandoned.

The invention provides a physiologically tolerable composition containing acesulfam, tabletting auxiliaries usual for sweetening agent tablets, and gelatin as dry binder. The composition is suitable for forming tablets by compression.

By acesulfam, there is to be understood in this context and hereinafter the free acid and the physiologically tolerable salts thereof.

Acesulfam is a sweetening agent of the formula

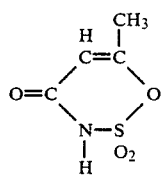

and is described in German Pat. No. 2,001,017.

The physical properties of acesulfam, that is, grain size, bulk volume and crystal shape, do not allow to manufacture tablets of sufficient quality without binder.

As all sweetening tablets, those containing acesulfam are required to be of sufficient mechanical stability (high break strength and low friability on mechanical strain) on the one hand, and on the other to be easily and transparently soluble even in cold beverages despite good mechanical stability.

Usually, a rapid dissolution of sweetening agent tablets is ensured in that the composition contains an acid and a soluble $CO_2$-yielding compound, that is, an effervescent mixture which dissolves in the presence of water with formation of $CO_2$.

It has already been described that the mechanical stability of tablets can be influenced by binders (see Voigt, *Lehrbuch der pharmazeutischen Technologie*, VEB Verlag Volk and Gesundheit, Berlin (1973), p. 180).

Gelatin is especially apt for the binder function, and moreover, it can be applied as a harmless auxiliary substance in food, for example in sweetening agent tablets. However, the use of gelatin in the manufacture of sweetening agent tablets is handicapped by the fact that according to the state of the art it is used as solution in moist granulation only (see Hager, *Handbuch der Pharmazeutischen Praxis*, 4th ed., vol, VII, p. 702, Springer Verlag, Berlin, Heidelberg, New York (1971); Voigt, loc. cit. pp. 160, 180, 181), and that moist granulation using water or an aqueous gelatin solution is generally impossible because of the content of $CO_2$-yielding compound and acid in the tablet mixture. It has been observed that moist granulation in the manufacture of acesulfam tablets causes considerable decomposition. Although moist granulation with organic solvents or a solution of gelatin in organic solvents is in principle feasible, it is not suitable because of the environmental strain involved and because of the expensive manufacturing process.

Surprisingly, it has now been observed that gelatin in pulverulent form (particle size less than 300 microns) functions as binder in a tablet mixture of acesulfam, sodium bicarbonate and optionally an acid, even in the very low concentration of 0.7%, which is below the normal concentration, when it is added in dry form. The mechanical stability of the tablets is improved and their decomposition time is not adversely affected.

The invention provides therefore a composition containing gelatin powder as dry binder in addition to acesulfam or a physiologically tolerable salt thereof, a water-soluble, $CO_2$-yielding compound and optionally a physiologically tolerable solid acid.

The compositions contain acesulfam preferably in the form of the free acid or the potassium salt. In the latter case, it is advantageous to add a further acid. Suitable physiologically tolerable acids are especially tartaric or citric acid. As $CO_2$-yielding compounds, there may be used sodium or potassium bicarbonate, magnesium carbonate, calcium bicarbonate or sodium glycolcarbonate, as well as mixtures of these compounds; sodium bicarbonate being preferred.

The dry binder gelatin is used in pulverulent form; the particle size being advantageously below 300 microns. The gelatin should have a quality in accordance with U.S. P XX. The content of gelatin in the composition is preferably from 0.4 to 5 weight %, the weight ratio of sweetening agent to sodium bicarbonate is 1:5, preferably from 1:1 to 1:2.

The composition of the invention can be compressed to tablets either after previous dry granulation or, when using suitable machines, directly.

The invention therefore provides also tablets containing the composition according to the invention, as well as a process for preparing these tablets. A tablet contains preferably 20 mg of sweetening agent, the total weight is preferably from 40 to 70 mg.

The process for the manufacture of the tablets comprises compressing the composition of the invention either directly or after previous dry granulation. It is preferably carried out as follows: the sweetening agent is mixed with the auxiliary(ies) ($CO_2$-yielding compound, acid), the mixture is subjected to a dry granulation, the granules are blended with the gelatin powder, and compressed to tablets. Alternatively, the sweetening agent can be mixed with the auxiliary(ies) and the gelatin powder, and the mixture can then be compressed directly to tablets.

The acesulfam "effervescent" tablets dissolve rapidly (see Table) and transparently in water, tea, coffee and other beverages despite the addition of dry binder. They are superior to binder-free tablets with respect to mechanical stability (see Table).

The following Examples illustrate the invention.

EXAMPLE 1

| | |
|---|---|
| (1) Acesulfam potassium | 20.0 mg |
| (2) sodium bicarbonate | 20.0 mg |
| (3) tartaric acid | 20.0 mg |
| (4) gelatin | 1.0 mg |
| | 61.0 mg |

Manufacture:

The substances (1) through (4) were mixed and directly compressed to give, for example, 5 mm biplane tablets. In comparison to tablets manufactured without gelatin, the resulting tablets were examined with respect to decomposition and lamination properties and to friability. The results are listed in the Table.

EXAMPLE 2

| | |
|---|---|
| (1) Acesulfam potassium | 20.0 mg |
| (2) sodium bicarbonate | 20.0 mg |
| (3) citric acid | 5.0 mg |
| (4) gelatin | 0.3 mg |
| | 45.3 mg |

Manufacture:

The substances (1), (2) and (3) were mixed, compacted and subsequently passed through a 0.8 mm sieve.

The granules so obtained were mixed with substance (4) and compressed to tablets having a diameter of 5 mm.

EXAMPLE 3

| | |
|---|---|
| (1) Acesulfam (free acid) | 20.00 mg |
| (2) sodium bicarbonate | 32.00 mg |
| (3) gelatin | 1.00 mg |
| | 53.00 mg |

The substances (1) through (3) were mixed and compressed to tablets having a diameter of 5 mm.

The test results are listed in the Table.

TABLE

| Tablets | acc. to Example 1 | Example 2 | Example 3 | Example 1, but without gelatin |
|---|---|---|---|---|
| decomposition time in water of 37° C. | 20–50″ | 20–50″ | 20–30″ | 20–50″ |
| lamination tendency | nonexistent | nonexistent | nonexistent | pronounced |
| friability(+) (Roche Friabilator) | 0–2% | 0–2% | 0–2% | 2–20% |
| number of broken tablets on friability test (using Roche Friabilator) | 0 | 0 | 0 | 2–20 |

(+) 20 tablets are subjected for 10 minutes to a rotation of about 24 rpm

What is claimed is:

1. A composition for a sweetening tablet, which comprises acesulfam or a physiological salt thereof as a sweetening agent, a water-soluble $CO_2$-yielding compound to provide effervescence and from 0.6 to 2 weight % of gelatin powder as dry binder.

2. The composition defined in claim 1, further comprising a physiologically tolerable solid acid.

3. The composition defined in claim 1, wherein the water-soluble $CO_2$-yielding compound is sodium bicarbonate.

4. The composition defined in claim 2, wherein the water-soluble $CO_2$-yielding compound is sodium bicarbonate.

5. An effervescent tablet which comprises an effective amount of a composition as defined in claim 1.

6. An effervescent tablet which comprises an effective amount of a composition as defined in claim 2.

7. A process for the manufacture of tablets according to claim 6 which comprises mixing acesulfam or a physiological salt thereof with a water-soluble $CO_2$-yielding compound and a gelatin powder to form a composition suitable for sweetening tablets, and compressing said composition to tablets directly.

8. A process for the manufacture of tablets according to claim 1 which comprises mixing acesulfam or a physiological salt thereof with a water-soluble $CO_2$-yielding compound to form a composition suitable for sweetening tablets, subjecting said composition to dry granulation, adding to said composition a gelatin powder to form a mixture, and compressing said mixture to form tablets.

9. A process for the manufacture of tablets according to claim 1 which comprises mixing acesulfam or a physiological salt thereof with a water-soluble $CO_2$-yielding compound, a gelatin powder and a physiologically tolerable solid acid to form a composition suitable for sweetening tablets, and compressing said composition to tablets directly.

10. A process for the manufacture of tablets according to claim 1 which comprises mixing acesulfam or a physiological salt thereof with a water-soluble $CO_2$-yielding compound and a physiologically tolerable solid acid to form a composition suitable for sweetening tablets, subjecting said composition to dry granulation, adding to said composition a gelatin powder to form a mixture, and compressing said mixture to form tablets.

* * * * *

UNITED STATES PATENT AND TRADEMARK OFFICE
CERTIFICATE OF CORRECTION

PATENT NO. : 4,552,771

DATED : November 12, 1985

INVENTOR(S) : Fulberth et al.

It is certified that error appears in the above-identified patent and that said Letters Patent is hereby corrected as shown below:

```
Column 4, line 19, (Claim 7, line 2), change "6" to --5--;
         line 25, (Claim 8, line 2), change "1" to --5--;
         line 33, (Claim 9, line 2), change "1" to --5--;
         line 40, (Claim 10, line 2), change "1" to --5--.
```

Signed and Sealed this

Eighteenth Day of March 1986

[SEAL]

Attest:

DONALD J. QUIGG

Attesting Officer     Commissioner of Patents and Trademarks